US009510601B2

(12) United States Patent
Takagi et al.

(10) Patent No.: US 9,510,601 B2
(45) Date of Patent: Dec. 6, 2016

(54) YEAST HAVING RESISTANCE TO FREEZING STRESS

(71) Applicant: NATIONAL UNIVERSITY CORPORATION NARA INSTITUTE OF SCIENCE AND TECHNOLOGY, Nara (JP)

(72) Inventors: Hiroshi Takagi, Nara (JP); Yu Sasano, Nara (JP); Jun Shima, Kyoto (JP); Yutaka Haitani, Kyoto (JP)

(73) Assignee: NATIONAL UNIVERSITY CORPORATION NARA INSTITUTE OF SCIENCE AND TECHNOLOGY, Nara (JP)

( * ) Notice: Subject to any disclaimer, the term of this patent is extended or adjusted under 35 U.S.C. 154(b) by 79 days.

(21) Appl. No.: 14/364,411

(22) PCT Filed: Nov. 20, 2012

(86) PCT No.: PCT/JP2012/080058
§ 371 (c)(1),
(2) Date: Jun. 11, 2014

(87) PCT Pub. No.: WO2013/088920
PCT Pub. Date: Jun. 20, 2013

(65) Prior Publication Data
US 2014/0377408 A1 Dec. 25, 2014

(30) Foreign Application Priority Data
Dec. 15, 2011 (JP) .................. 2011-274519

(51) Int. Cl.
| G01N 33/53 | (2006.01) |
| C12N 13/00 | (2006.01) |
| A21D 8/04 | (2006.01) |
| C07K 14/395 | (2006.01) |
| C12N 1/04 | (2006.01) |
| C12N 1/18 | (2006.01) |
| C12N 15/81 | (2006.01) |

(52) U.S. Cl.
CPC ............ *A21D 8/047* (2013.01); *C07K 14/395* (2013.01); *C12N 1/04* (2013.01); *C12N 1/18* (2013.01); *C12N 15/81* (2013.01)

(58) Field of Classification Search
None
See application file for complete search history.

(56) References Cited

U.S. PATENT DOCUMENTS 5,352,606 A * 10/1994 Takano ................. A21D 8/047
426/18

FOREIGN PATENT DOCUMENTS

| EP | 0 921 190 | 6/1999 |
| JP | 9-234058 | 9/1997 |
| JP | 11-169180 | 6/1999 |
| JP | 2001-238665 | 9/2001 |
| JP | 2006-67806 | 3/2006 |
| JP | 2008-148688 | 7/2008 |
| JP | 2010-183887 | 8/2010 |
| JP | 2013-118851 | 6/2013 |

OTHER PUBLICATIONS

Notification of Transmittal of Translation of the International Preliminary Report on Patentability issued Jun. 26, 2014 in corresponding International Application No. PCT/JP2012/080058.
Attfield, P., "Stress Tolerance: The Key to Effective Strains of Industrial Baker's Yeast", Nature Biotechnology, vol. 15, pp. 1351-1357 (1997).
Du, X., et al., "N-Acetyltransferase Mpr1 Confers Ethanol Tolerance on *Saccharomyces cerevisiae* by Reducing Reactive Oxygen Species", Appl. Microbiol. Biotechnol., vol. 75, pp. 1343-1351, (2007).
Du, X., et al., "N-Acetyltransferase Mpr1 Confers Freeze Tolerance on *Saccharomyces cerevisiae* by Reducing Reactive Oxygen Species", J. Biochem., vol. 138, pp. 391-397, (2005).
Normura, M. et al., "Role of the Yeast Acetyltransferase Mpr1 in Oxidative Stress: Regulation of Oxygen Reactive Species Caused by a Toxic Proline Catabolism Intermediate", Proc. Natl. Acad. Sci. U.S.A., vol. 101, pp. 12616-12621, (2004).
Shima, J., et al., "Possible Roles of Vacuolar H$^+$-ATPase and Mitochondrial Function in Tolerance to Air-Drying Stress Revealed by Genome-wide Screening of *Saccharomyces cerevisiae* Deletion Strains", Yeast. vol. 25, pp. 179-190, (2008).
Makrantoni, V., et al., "A Novel Role for the Yeast Protein Kinase Dbf2p in Vacuolar H$^+$-ATPase Function and Sorbic Acid Stress Tolerance", Microbiology, vol. 153, pp. 4016-4026, (2007).
Ando, A., et al., "Identification and Classification of Genes Required for Tolerance to High-Sucrose Stress Revealed by Genome-wide Screening of *Saccharomyces cerevisiae*", FEMS Yeast Res, vol. 6, pp. 249-267, (2006).
Ando, A., et al., "Identification and Classification of Genes Required for Tolerance to Freeze-thaw Stress Revealed by Genome-wide Screening of *Saccharomyces cerevisiae* Deletion Strains", FEMS Yeast Res, vol. 7, pp. 244-253, (2007).
Leza, M. et al., "POG1, A Novel Yeast Gene, Promotes Recovery From Pheromone Arrest via the G1 Cylin CLN2", Genetics, vol. 151(2), pp. 531-543, (1999).
Demae, M., et al., "Overexpression of Two Transcriptional Factors, Kin28 and Pog1, Suppresses the Stress Sensitivity Caused by the rsp5 mutation in *Saccharomyces cerevisiae*", FEMS Microbiology Letters, vol. 277, No. 1, pp. 70-78, (2007).
Extended European Search Report dated Jul. 10, 2015, issued in corresponding European Patent Application No. 12857491.0.

(Continued)

*Primary Examiner* — Jennifer Graser
(74) *Attorney, Agent, or Firm* — Wenderoth, Lind & Ponack, L.L.P.

(57) ABSTRACT

The present invention provides yeast having increased resistance to freezing stress in which POG1 gene is inactivated, a method for producing such yeast, and a method for using such yeast in food production.

2 Claims, 4 Drawing Sheets

(56) References Cited

OTHER PUBLICATIONS

Jun Shima et al., "Stress-tolerance of baker's-yeast (*Saccharomyces cerevisiae*) cells: stress-protective molecules and genes involved in stress tolerance", Biotechnol. Appl. Biochem., vol. 53, No. 3, May 29, 2009, pp. 155-164.

Yu Sasano et al., "Improvement of fermentation ability under baking-associated stress conditions by altering the *POG1* gene expression in baker's yeast", International Journal of Food Microbiology, vol. 165, No. 3, May 28, 2013, pp. 241-245.

* cited by examiner

YEAST HAVING RESISTANCE TO FREEZING STRESS

TECHNICAL FIELD

The present invention relates to a field of breeding yeast. Further, the present invention relates to baker's yeast having high resistance to freezing stress, a method for producing said yeast, a bread dough produced by use of said yeast, a method for producing bread, and products produced by said method.

BACKGROUND ART

Bread production process needs dough expansion by baker's yeast. In order to provide bread having a certain quality, strict control of the fermentation of baker's yeast, *Saccharomyces cerevisiae* is necessary. Baker's yeast cells are exposed to many ambient stresses such as freezing, drying, high temperature and high osmotic pressure in the bread production process (Non-patent reference 1). These ambient stresses weaken fermentation ability of yeast. Therefore, it is desired to establish a technique for the production of a yeast strain having high resistance to ambient stresses. Recently, a bread production method using frozen dough has been rapidly become popular, and it is particularly desired to produce a yeast strain having resistance to freezing stress given by said method.

In the fields of bread production and yeast production, ambient stresses which are given to yeast and restrict the fermentation in bread production have been investigated. Many trials for solving the problems have been done by production of yeast having resistance to these ambient stresses.

On the other hand, as findings on stress-resistant mechanisms have been accumulated, trials for reinforcing resistance have been done by modifying genes relating to resistance.

For example, an amino acid, proline has an action to protect yeast from stresses such as freezing, drying and oxidation (Patent reference 1). It is known that a yeast strain, which lacks a PUT1 gene encoding proline oxidase and expresses a mutant PRO1 gene encoding a gamma-glutamyl kinase variant, accumulates proline in the cell, thereby the strain becomes resistant to ethanol (Patent reference 2).

It is also known that N-acetyl transferase Mpr1 protects yeast from oxidative stresses such as heat shock, hydrogen peroxide treatment, ethanol and low temperature stress (Non patent references 2-4) and that yeast efficiently expressing a mutant Mpr1 has resistance to drying and a high temperature (Patent reference 3).

In addition, it is known, for example: deletion of CBS2 gene causes sensitivity to drying stress (Non patent reference 5); destruction of DBF2 gene causes a high sensitivity to a sorbitol stress (Non patent reference 6); Resistance to high sucrose stress is remarkably lost in a strain in which an aromatic amino acid synthesis-related gene (for example, ARO1, etc.) is disrupted; in a strain in which BUD23, GON7 and SPT20 genes are disrupted, a sensitivity to a high sucrose stress is increased (Non patent reference 7); and in a strain in which OCA1 gene or OCA2 gene (encoding a phosphatase catalyzing dephosphorylation of a phosphorylayted protein), or ALD2 gene is disrupted, resistance to high sucrose stress is increased (Patent reference 4).

Regarding freezing stress, it is known, for example: in a strain in which ATH1 gene encoding an acidic trehalase is disrupted, resistance to freezed dough stress and resistance to high sucrose stress are increased (Patent reference 5); in a strain in which CAR1 gene encoding an arginase is disrupted, amino acids having high polarity are accumulated in the cells and resistance to freezing stress is increased (Patent reference 6); and in a strain in which PMR1 gene or SNF5 gene is disrupted, resistance to freezing stress is lost (Non patent reference 8).

REFERENCES

Patent References

Patent reference 1: JP H09-234058 A
Patent reference 2: JP 2006-067806 A
Patent reference 3: JP 2010-183887 A
Patent reference 4: JP 2008-148688 A
Patent reference 5: JP H11-169180 A
Patent reference 6: JP 2001-238665 A

Non Patent References

Non Patent reference 1: Attfield, Nat. Biotechnol. 15: 1351-1357 (1997)
Non Patent reference 2: Du and Takagi, Appl. Microbiol. Biotechnol. 75: 1343-1351 (2007)
Non Patent reference 3: Du and Takagi, J. Biochem. 138: 391-397 (2005)
Non Patent reference 4: Nomura and Takagi, Proc. Natl. Acad. Sci. U.S.A. 101: 12616-12621 (2004)
Non Patent reference 5: Shima et al., Yeast (2008) 25: 179-190
Non Patent reference 6: Makrantoni at al., Microbiology 153: 4016-4026 (2007)
Non Patent reference 7: Ando et al., FEMS Yeast Res 6: 249-267 (2006)
Non Patent reference 8: Ando et al., FEMS Yeast Res 7: 244-253 (2007)

DISCLOSURE OF INVENTION

Problem to be Solved by the Invention

However, researches for baker's yeast having resistance to stress are not sufficient. Therefore, it is strongly desired to find genes taking part in resistance to stress, and to develop yeast having higher resistance to stress or a method for breeding such yeast.

The present invention was carried out in view of the above problems. The purpose of the present invention is to provide yeast which can maintain sufficient fermentation ability under freezing condition which is an ambient stress such as in a method for the production of bread using frozen dough, that is, to provide yeast having sufficiently high resistance to freezing stress, to provide a method for breeding such yeast, and to provide a method for producing bread dough and bread using such yeast.

Means to Solve the Problem

The inventors focused on POG1 gene. It is known in a yeast strain for laboratory use that a strain overexpressing POG1 gene shows a phenotype of lithium chloride resistance (Demae et al., FEMS Microbiol. Lett., 277, 70-78 (2007)). The inventors found that resistance of yeast to freezing stress can be increased by inactivation of POG1 gene in yeast, and accomplished the present invention. That is, the present invention relates to:

(1) Yeast having increased resistance to freezing stress, in which POG1 gene is inactivated.

(2) The yeast according to (1), wherein POG1 gene consists of any one of the polynucleotides:

(a) a polynucleotide encoding an amino acid sequence of SEQ ID NO: 1;

(b) a polynucleotide encoding a protein having a homology of 80% or more to an amino acid sequence of SEQ ID NO: 1;

(c) a polynucleotide encoding a protein consisting of an amino acid sequence of SEQ ID NO: 1 in which one, or several or more amino acid residues are deleted, substituted, inserted and/or added;

(d) a polynucleotide consisting of a nucleotide sequence of SEQ ID NO: 2;

(e) a polynucleotide which hybridizes under a stringent condition to a polynucleotide consisting of a nucleotide sequence complementary to any polynucleotide of (a)-(d).

(3) The yeast according to (1) or (2), which is baker's yeast.

(4) A method for producing bread dough, comprising using the yeast according to any one of (1)-(3).

(5) A method for producing bread, comprising using the yeast according to any one of (1)-(3).

(6) A method for producing yeast having increased resistance to freezing stress, comprising a step of inactivating POG1 gene.

(7) The method according (6), wherein POG1 gene consists of any one of the polynucleotides:

(a) a polynucleotide encoding an amino acid sequence of SEQ ID NO: 1;

(b) a polynucleotide encoding a protein having a homology of 80% or more to an amino acid sequence of SEQ ID NO: 1;

(c) a polynucleotide encoding a protein consisting of an amino acid sequence of SEQ ID NO: 1 in which one, or several or more amino acid residues are deleted, substituted, inserted and/or added;

(d) a polynucleotide consisting of a nucleotide sequence of SEQ ID NO: 2;

(e) a polynucleotide which hybridizes in a stringent condition to a polynucleotide consisting of a nucleotide sequence complementary to any polynucleotide of (a)-(d).

(8) The method according to (6) or (7), further comprising a step of comparing resistance to freezing stress of yeast in which POG1 gene is inactivated with that of yeast in which POG1 gene is not inactivated.

(9) The method according to (8), further comprising a step of selecting yeast having increased resistance to freezing stress.

Effect of the Invention

The present invention enables to easily obtain a yeast strain having higher resistance to freezing stress. Further, the present invention also enables to easily make a yeast strain to be a resistant strain to freezing stress. Therefore, the yeast of the present invention is suitable for the production of frozen bread dough and so on.

DETAILED DESCRIPTION OF THE INVENTION

Figure 1:
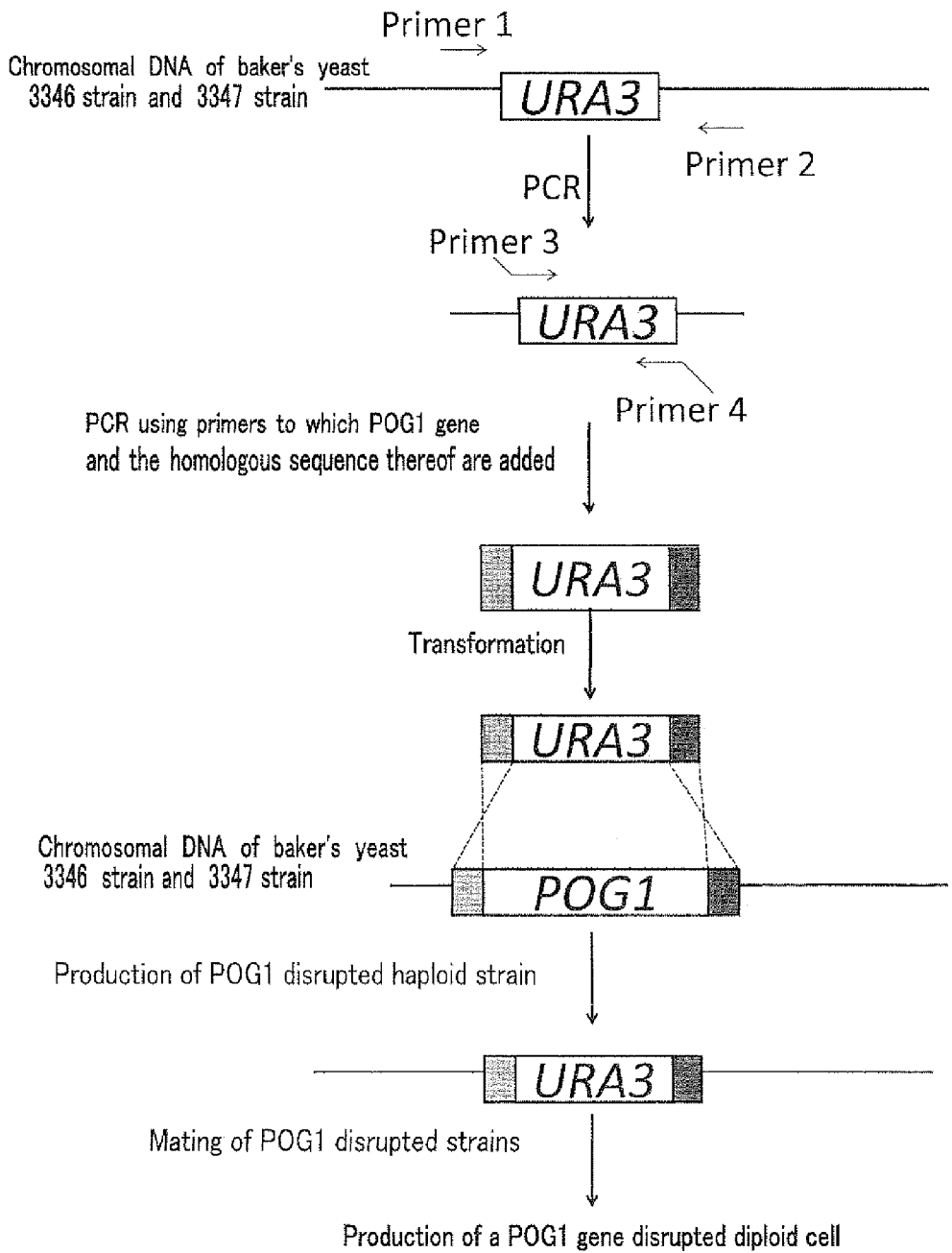
FIG. 1 shows a scheme of a method for producing a strain in which POG1 gene is disrupted.
Figure 2:
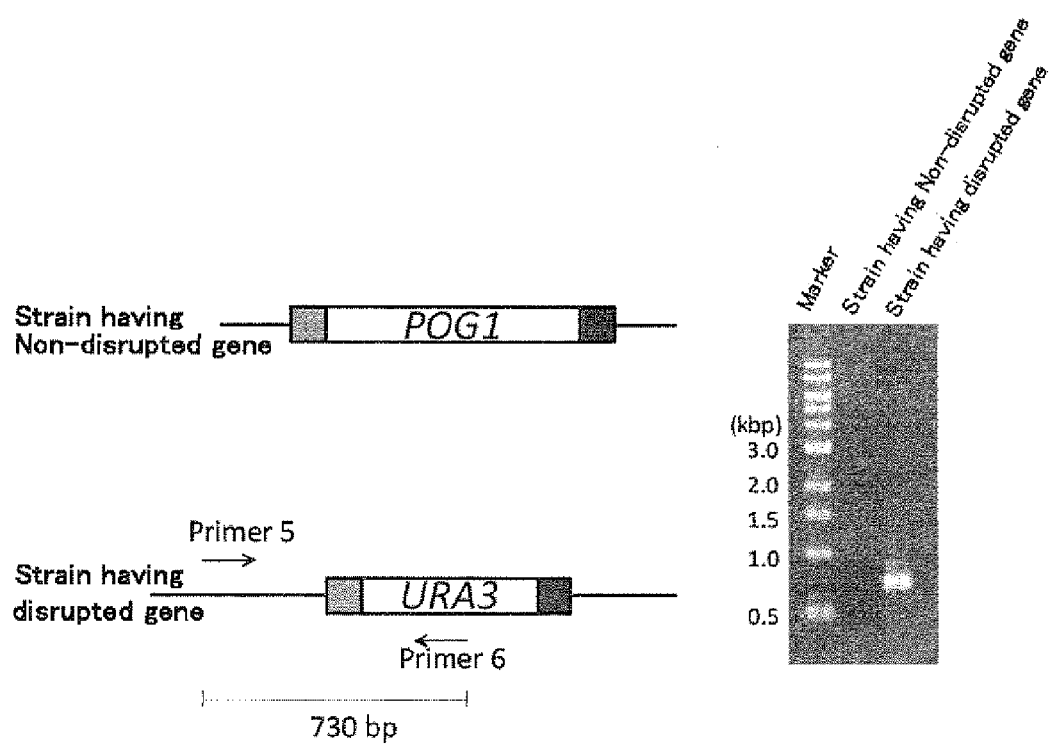
FIG. 2 shows experimental results of confirmation of the production of a strain in which POG1 gene is disrupted.

The embodiments of the present invention are described below. All the scientific articles and patent documents are incorporated herein by reference. Unless particularly defined herein, a numerical range "A-B" means "A or more and B or less".

As used herein, bases and amino acids are described using one letter system or three letters system defined by IUPAC and IUB. As used herein, the term "protein" is used interchangeably as "peptide" or "polypeptide". In addition, the term "polynucleotide" is used interchangeably as "gene", "nucleic acid" or "nucleic acid molecule", and intended a polymer of nucleotides. Here, a gene can exist in a form of a DNA (for example a cDNA or a genomic DNA) or an RNA (for example a mRNA). A DNA or an RNA may be single-stranded or double-stranded. A single-stranded DNA or RNA may be a coding strand (a sense strand) or a non-coding strand (an antisense strand). In addition, a gene may be chemically synthesized, and codon usage may be changed to enhance expression of the encoded protein. Of course, a codon can be also substituted by another codon in case that they encode a same amino acid. Moreover, a gene, which encodes a protein, includes a nucleotide sequence having any nucleotide sequence based on degeneracy of genetic codes.

1. DEFINITION OF THE TERMS

Definitions of the terms particularly used in the specification are recited below.

As used herein, "yeast" refers to fungus which passes most of its lifecycle as a monocellular state. Examples of typical yeast are those belonging to genus *Saccharomyces* and *Schizosaccharomyces*; in particular, *Saccharomyces cerevisiae, Saccharomyces ludwigii* and *Scizosaccharomyces pombe*.

As used herein, "baker's yeast" refers to yeast belonging to *Saccharomyces cerevisiae* which is used in the production of bread.

As used herein, the term "sucrose concentration (%)" refers a relative concentration of sucrose to flour in a material to be fermented, unless the unit is specified. In particular, the term refers to grams of sucrose added to 100 g of flour.

As used herein, "freezing stress" refers that yeast is frozen at 0° C. or lower temperature. So long as yeast is frozen, any temperature of 0° C. or lower can be used. In addition, "resistance to freezing stress" refers to the character of yeast which shows higher fermentation ability than the wild type yeast under freezing stress condition. Typically, whether mutant yeast has resistance to freezing stress or not is determined using fermentation ability under freezing stress as an indicator which is measured by the amount of produced carbon dioxide gas.

As used herein "fermentation ability" refers to an ability to produce metabolic products as a result of anaerobical degradation of sugars when yeast is cultured. Typically, fermentation by yeast includes, but not limited to, alcohol fermentation, glycerol fermentation, and so on. As for an index showing fermentation ability, a method using a machine, fermograph can be used which measures an amount of carbon dioxide gas produced from yeast in bread dough to determine the fermentation ability of the bread dough. As the unit therefore, for example, ml/100OD$_{600}$ can be used which is an amount of carbon dioxide gas produced by yeast, OD$_{600}$ of which is 100, but not limited to it. Other indices than the above include, but not limited to, fermentation ability under a low sugar condition (F10), fermentation ability under a high sugar condition (F40), and maltose fermentation ability (Fm), and so on.

As used herein, "dough" includes not only materials submitted to bread fermentation but also "seed dough" added to bread dough. As used herein, the term "seed dough" refers to a seed (a starter) added for the fermentation of bread dough which contains yeast necessary for the fermentation and at least a part of blended materials.

As used herein, "fermentation" refers to a phenomenon where at least a part of blended materials is degraded by yeast.

As used herein, "inactivation" of a gene means that an inherent function of a gene or a polypeptide encoded by the gene is decreased or deactivated, using a technique of genetic engineering or biotechnology such as gene disruption (for example, Methods in enzymology, 194, 281-301 (1991)), introduction of a transposon into the gene (for example, Methods in enzymology, 194, 342-361 (1991)), introduction of an antisense gene of the gene and expression thereof (for example, JP-A 7-40943, and 23rd European Brewery Conv. Proc., 297-304 (1991)), introduction of a DNA which participates in silencing into a site near the gene (for example, Cell, 75, 531-541 (1993)), treatment by an antibody to a polypeptide encoded by the gene (for example, European J. Biochem., 231, 329-336 (1995)), and so on.

As used herein, "a stringent condition" refers to a condition where a double stranded polynucleotide specific to a nucleotide sequence is formed and a double stranded polynucleotide which is not specific to the nucleotide sequence is not formed. In other words, it can be said that "a stringent condition" is a condition where nucleic acids having a high homology hybridize each other in a temperature range of between a fusion temperature (Tm value) of a completely matched hybrid and a temperature lower than the Tm value by 15° C., preferably by 10° C., more preferably 5° C. For example, a hybridization condition of 68° C., for 20 hours in a general buffer solution for hybridization can be recited. As an example, a condition where hybridization is done at 60-68° C., preferably 65° C., more preferably 68° C., for 16-24 hours in a buffer solution consisting of 0.25M Na$_2$PO$_4$, pH 7.2, 7% SDS, 1 mM EDTA, 1×Denhardt's solution, and washed twice for 15 minutes, at 60-68° C., preferably 65° C., more preferably 68° C., in a buffer solution consisting of 20 mM Na$_2$PO$_4$, pH 7.2, 1% SDS, 1 mM EDTA can be recited. As another example, the following condition is recited: pre-hybridization is done at 42° C., overnight in a buffer solution comprising 25% formamide (50% formamide in a more stringent condition), 4×SSC (sodium chloride/sodium citrate), 50 mM HEPES, pH 7.0, 10×Denhardt's solution, 20 µg/ml denatured salmon sperm DNA, thereafter hybridization is done by adding a labeled probe and keeping at 42° C. overnight. As a washing solution and a temperature condition for the washing thereafter, the following conditions are exemplified: a condition of, or a condition near "1×SSC, 0.1% SDS, 37° C.", and a condition of, or a condition near "0.5×SSC, 0.1% SDS, 42° C." as a more stringent condition, and "0.2×SSC, 0.1% SDS, 65° C." as a still more stringent condition. Thus, as the stringency of washing condition in hybridization increases, it can be more expected that a DNA is isolated which has a higher homology to the probe sequence. It should be noted that the above conditions for SSC, SDS and temperature are examples. A skilled person in the art can attain the above stringencies by combining the above factors and other factors which determine the stringency of hybridization such as probe concentration, probe length, hybridization reaction period, and so on. For example, a skilled person in the art can easily obtain desired genes by referring to Molecular Cloning (Sambrook and Russell, Molecular Cloning: A Laboratory Manual 3rd ed., Cold Spring Harbor Laboratory Press, Woodbury, N.Y. (2001), and so on.

As used herein, "homology" (of a nucleotide sequence and amino acid sequence, etc.) refers to an extent of identity of between two or more sequences. In addition, as used herein, "identity" (of a nucleotide sequence and amino acid sequence, etc.) refers to an extent of sequence identity of each nucleic acid or amino acid, etc. between two or more sequences which can be compared. Therefore, as homology of two genes is higher, identity or similarity of their sequences is higher. "Similarity" refers to an extent of identity in a sense of the above defined homology between two or more gene sequences when conservative substitutions are considered as identical. Whether two kinds of genes have any homology can be determined by direct comparison of the sequences, or using a hybridization method under a stringent condition in case of nucleic acids. Comparison of identity and homology of amino acid sequences and nucleotide sequences can be determined by use of tools for sequence analysis such as PASTA and BLAST.

2. YEAST HAVING INCREASED RESISTANCE TO FREEZING STRESS

In yeast according to the present invention, POG1 gene is inactivated. POG1 gene, when expected from its DNA sequence, encodes a protein pog1 having a molecular weight of about 39 kDa. It has been reported that the protein involves the control of cell cycle of yeast as a transcription factor (Maria, A. et al., Genetics, 151; 531-543 (1999)). However, the function of the protein is still unknown because any DNA motif characteristic of a transcription factor is not found in the amino acid sequence of the protein, and it is not reported that the protein actually controls transcription of a gene. Moreover, any gene having a homology in a level of a deduced amino acid sequence has not been found not only in yeast but also all living species. POG1 gene was obtained as a multi copy suppressor which complements the stress sensitivity of an ubiquitin ligase Rsp5 mutant strain of yeast, and it is known that an experimental strain overexpressing the gene shows a lithium chloride resistant phenotype (Damae et al., FEMS Microbiol. Lett., 277, 70-78 (2007)). However, it is quite unexpected that resistance to freezing stress is improved by the inactivation of POG1 gene.

POG1 gene includes gene as defined above, and consists of the following polynucleotides, but not limited to:

(a) a polynucleotide encoding an amino acid sequence of SEQ ID NO: 1;

(b) a polynucleotide encoding a protein having a homology of 80% or more to an amino acid sequence of SEQ ID NO: 1;

(c) a polynucleotide encoding a protein consisting of an amino acid sequence of SEQ ID NO: 1 in which one, or several or more amino acid residues are deleted, substituted, inserted and/or added;

(d) a polynucleotide consisting of a nucleotide sequence of SEQ ID NO: 2; or (e) a polynucleotide which hybridizes under a stringent condition to a polynucleotide consisting of a nucleotide sequence complementary to any nucleotide of (a)-(d).

The polynucleotide of above (b) encodes a protein having at least a certain homology to an amino acid sequence of SEQ ID NO: 1. At least a certain homology refers to a homology of at least 80% or more, preferably 85% or more, more preferably 90% or more, still more preferably 95%, 96%, 97%, 98%, 99%, 99.5% or more.

The number of amino acids which may be deleted from, substituted in, or added to the polynucleotide of above (c) is not limited so long as the function thereof is not lost, and refers to the number or so which may be deleted, substituted or added by a known method for mutagenesis such as site-directed mutagenesis. Usually, the number is 30 amino acids or less, preferably 20 amino acids or less, more preferably 10 amino acids or less, most preferably 5 amino acids or less (for example, 5, 4, 3, 2, or 1 amino acids). Whether the desired character is conferred to yeast by a protein to which a mutation is introduced can be confirmed by determining whether the gene encoding the protein is inactivated, and the resistance of the yeast to freezing stress is increased or not. Further, as used herein, "mutation" mainly means a mutation introduced artificially by site-directed mutagenesis, however mutation may be a similar one which occurs spontaneously.

It is preferable that an amino acid residue is mutated to another amino acid residue in which the character of the side chain is conserved. For example, characters of side chains of amino acids can be recited: hydrophobic amino acids (A, I, L, H, F, P, W, Y, V), hydrophilic amino acids (R, U, N, C, F, Q, G, H, K, S, T), amino acids having a aliphatic side chain (G, A, V, L, I, P), amino acids having a side chain containing hydroxyl group (S, T, Y), amino acids having a side chain containing a sulfur atom (C, M), amino acids having a side chain containing a carboxylic acid or an amide (D, N, E, Q), amino acids having a side chain containing a base (R, K, H), amino acids having a side chain containing an aromatic moiety (H, F, Y, W). Further, it is well known that amino acids are classified according to mutational matrix (Taylor, J. Theor. Biol. 119, 205-218 (1986); Sambrook and Russell, Molecular Cloning 3rd ed. A7.6-A7.9, Cold Spring Harbor Laboratory Press, 2001). This classification is summarized: aliphatic amino acids (L, I, V), aromatic amino acids (H, W, Y, F), charged amino acids (D, E, R, K, H), positively charged amino acids (R, H), negatively charged amino acids (D, E), hydrophobic amino acids (H, W, Y, F, M, L, I, V, C, A, G, T, K), polar amino acids (T, S, N, D, E, Q, R, K, H, W, Y), small amino acids (P, V, C, A, G, T, S, N, D), micro amino acids (A, G, S), and large (non-small) amino acids (Q, E, R, K, H, W, Y, F, M, L, I). Here, one letter description of amino acids is used in the above parentheses.

It has been already known that a polypeptide having an amino acid sequence which is modified by deletion of one or several amino acid residues, addition of one or several amino acid residues, and/or substitution by other amino acid residues maintains its biological activity. Further, it is more preferable that the target amino acid residue is mutated to an amino acid residue having as many common characters as possible.

Further, in homology the polynucleotide of above (e) has a sequence identity of at least 80% or more, preferably 85% or more, more preferably 90% or more, still more preferably 95%, 96%, 97%, 98%, 99% or more to the polynucleotide of above (d) (the nucleotide sequence of SEQ ID NO: 2).

Preferably, yeast belongs to, but not limited to, *Saccharomyces cerevisiae*, more preferably baker's yeast, still more preferably diploid baker's yeast.

As shown in examples, such yeast has resistance to freezing stress, and has increased fermentation ability in the presence of freezing stress, compared with the wild type strain in which POG1 gene is not inactivated.

Further, yeast having increased resistance to freezing stress according to the present invention may be yeast in which POG1 gene is inactivated by spontaneous mutation.

3. A METHOD FOR PRODUCING YEAST HAVING INCREASED RESISTANCE TO FREEZING STRESS

The method for producing the yeast having increased resistance to freezing stress according to the present invention comprises a step of inactivating POG1 gene using gene recombination technology.

Basic operations of gene engineering and biotechnology used for the inactivation of POG1 gene can be performed according to the methods described in commercial textbook of experiments such as Molecular Cloning, Cold Spring Harbor Laboratory (1982), Molecular Cloning: A laboratory Manual 3rd ed., Cold Spring harbor Laboratory Press, Woodbury, N.Y. (2001), Methods in Enzymology, 194 (1991), Jikken Igaku Bessatu, Koubo niyoru Idensi JikkenHou, Youdosha (1994) and so on.

Methods for inactivating POG1 gene in yeast may be any method so long as the methods are for decreasing or inactivating the function of POG1 gene or the protein encoded by POG1 gene, and include disruption of a gene (for example, Methods in Enzymology, 194, 281-301 (1991)), introduction of a transposon into a gene (for example, Methods in Enzymology, 194, 342-361 (1991)), introduction of an antisense gene of a gene and its expression (for example, JP-A 7-40943, and 23rd European Brewery Conv. Proc., 297-304 (1991)), introduction of a DNA which participates in silencing into a site near a gene (for example, Cell, 75, 531-541 (1993)), treatment by an antibody to a polypeptide encoded by a gene (for example, European J. Biochem., 231, 329-336 (1995)), and so on.

Yeast used for inactivation of POG1 gene belongs to, but not limited to, preferably *Saccharomyces cerevisiae*, more preferably baker's yeast.

Disruption of POG1 gene means that a DNA which has a nucleotide sequence homologous to POG1 gene but is unable to function as POG1 gene on account of mutation such as addition, deletion and substitution is introduced into yeast cells to cause homologous recombination and make the mutation incorporated into the gene on genome.

Methods for production of a DNA used for gene disruption include, for example, a method where a gene which complements low temperature sensitivity is cut by a restriction enzyme to cause addition, deletion, substitution and so on of a DNA, or a method where a gene which complements low temperature sensitivity is mutated in vitro (in vitro mutagenesis). For example, a method for inserting a marker gene may be used for addition or substitution of a gene.

In order to disrupt POG1 gene, any site may be disrupted, for example, a promoter site of POG1 gene, an open reading frame (ORF) site, and a terminator site, or combination thereof may be disrupted. Gene disruption can also be carried out by deleting whole POG1 gene.

POG1 gene can be disrupted, for example, by transforming a plasmid or a fragment thereof for disrupting POG1 gene is transformed into yeast, and causing homologous recombination of the DNA fragment contained in the transformed plasmid or fragment thereof with the gene on yeast genome. In case that a plasmid for disruption of POG1 gene or a fragment thereof and POG1 gene on yeast genome have a homology to an extent for causing homologous recombination, homologous recombination is caused. Whether a DNA fragment can cause homologous recombination can be confirmed by introducing the fragment into yeast, and determining whether any strain in which homologous recombination has been caused can be isolated, that is, whether the fermentation ability shows resistance to freezing stress.

A vector used for preparing a plasmid for disrupting POG1 gene includes, not limited to, a vector which can be maintained in yeast such as YEp, YCp, YIp, and a vector which can be maintained in *E. coli* such as pGEM-T, pUC, pBluescript.

A marker gene includes any marker gene which can be used in yeast, for example, a gene which complements an auxotrophic mutation such as URA3, TRP1, LEU2, HIS3, and a resistant gene to a chemical substance such as G418, hygromycin B, cerulenin, p-fluorophenylalanine (for example, J. Ferment. Bioeng., 76, 60-63 (1993), Enzyme and Microb. Technol., 15, 874-876 (1993)), and so on.

POG1 gene on the genome of yeast can be disrupted by transforming yeast with a plasmid for disruption of POG1 gene. Transformation of yeast can be performed by a method usually used in the field of gene engineering or biotechnology such as spheroplast method (Proc. Natl. Acad, Sci. USA, 84, 1929 (1978), lithium acetate method (J. Bacteriol., 153, 163 (1983)), electroporation method (Methods Enzymol., 194, 182 (1990)) and so on.

A transformant can be easily isolated by introducing a marker gene into a plasmid for disruption of POG1 gene, and using the marker as an indicator. In addition, fermentation ability increases under freezing stress when POG1 gene on the genome of yeast is disrupted, thereby a transformant can be isolated. Resistance to freezing stress of a strain where POG1 gene has been disrupted can be confirmed by determining fermentation ability of the yeast under freezing stress.

It is preferable to produce a POG1 gene disrupted strain as above mentioned by self-cloning technology using genes all of which are derived from yeast and which do not contain any foreign genes because yeast produced by self-cloning technology can be treated similarly to usual microorganisms for food production. For accomplishing self-cloning technology, a marker gene such as URA3 which is introduced is preferably a gene from *Saccharomyces cerevisiae*, particularly from baker's yeast.

In addition, a POG1 gene disrupted strain can be obtained by selecting from yeast strains which have been submitted to a mutation treatment. That is, in the method of the present invention, POG1 gene may be disrupted by a mutation treatment. Methods for a mutation treatment include, but not limited to, physical mutation treatments such as UV irradiation and application of radiation, and chemical mutation treatments with a mutagen such as ethyl methanesulfonate and so on. A POG1 gene disrupted strain can be selected from mutants obtained by a mutation treatment using the increase of fermentation ability under freezing stress as an indicator.

Yeast the present invention is preferably a diploid. A diploid homozygote mutant of POG1 gene can be obtained by a method well known in the art. For example, the method includes, but not limited to, (1) a method where a haploid mutant of POG1 gene is produced from a different zygotic haploid (a type and alpha type), and a diploid mutant is produced by crossing these haploids; and (2) a method using two different markers where a mutation is introduced into a first allelic gene using a first selection marker, thereafter a mutation is introduced into a second allelic gene using a second selection marker.

By the operations as mentioned above, yeast in which resistance to freezing stress is increased can be produced.

4. A METHOD FOR PRODUCING BREAD DOUGH, AND A METHOD FOR PRODUCING BREAD

The yeast of the present invention has an inactivated POG1 gene, and is particularly very excellent in resistance to freezing stress in frozen bread dough. Therefore, the baker's yeast of the present invention is sufficiently resistant to freezing stress in frozen bread dough, and well exerts its ability in the fermentation, and various bread having delicious taste can be produced when baked. The frozen dough of the present invention can be produced according to a conventional method except that the yeast having increased resistance to freezing stress in which POG1 gene is inactivated is used. Bread can also be produced according to a conventional method except that the yeast having increased resistance to freezing stress in which POG1 gene is inactivated is used.

The present invention is not limited to the scope as described above. Variations of the present invention are also within the scope disclosed herein. Embodiments obtained by appropriately combining different embodiments disclosed herein are also within the scope of the present invention. All documents cited herein are incorporated herein by reference. The present invention is further described in detail by showing examples below. However it should not be construed that the scope of the present invention is limited to only the scope of the examples.

Examples

The present invention is further described in detail by showing examples below. However it should not be construed that the scope of the present invention is limited to only the scope of the examples.

(1) Production of POG1 Gene Disrupted Diploid Yeast Using Yeast for Practical Use:

FIG. 1 shows a scheme of production of a POG1 gene disrupted strain. URA3up-Fw primer having a nucleotide sequence (CTAGGGAAGACAAGCAACGAAACG: SEQ ID NO: 3) as a forward primer and URA3down-Rv primer having a nucleotide sequence (GGGCGGGTTATCAGAT-ATTATCAGG: SEQ ID NO: 4) as a reverse primer were used to amplify URA3 gene region. URA3 gene region was amplified using these primers and chromosomal DNA of baker's yeast of Saccharomyces cerevisiae as a template. The amplified fragment was used as a template, and POG1 URA3-Fw primer having a nucleotide sequence (CCT-GCGCTTAACTCATACAAAAAGGCG-CAAAACATTTCAAGAGTCCCACGATTAATTG CAGAAATTGAAAgattcggtaatctccgag: SEQ ID NO: 5) as a forward primer to 5' terminal of which a part of POG1 gene is added and POG1+URA3-Rv primer having a nucleotide sequence (TGAACTGAAGTAAGGTGGACGGATG-CATCGAATGAAGGTTAGGAAGGGATATAGTTTT AGAAATTAGGTGgtaataactgatataattaaattg: SEQ ID NO: 6) as a reverse primer to 5' terminal of which a part of POG1 gene is added were used to amplify a fragment for disruption of POG1 gene. The amplified fragment was transformed into haploid uracil auxotrophic strains of baker's yeast (3346 Ura3⁻, 3347 Ura3⁻), and a POG1 gene disrupted strain was isolated using uracil non-auxotrophy as an indicator. Completion of the production of a POG1 gene disrupted strain was confirmed by PCR using POG1upstream-Fw primer (TTAAAGGCTACGCAGAAGAGG: SEQ ID NO: 7) and URA3ORF-Rv primer (GGCCTCTAGGTTCCTTT-GTTACTTC: SEQ ID NO: 8). The POG1 gene disrupted strains produced in an a type and an alpha type haploids respectively were mated to produce a diploid strain. Completion of the production of the diploid strain was confirmed by spore formation on a sporulation medium (0.05% glucose, 0.1% yeast extract, 1% potassium acetate, 2% agar).

(2) Resistance to Freezing Stress of POG1 Gene Disrupted Diploid Yeast.

Resistance to freezing stress of the mutant strain produced in Example 1 was estimated.

Figure 3:
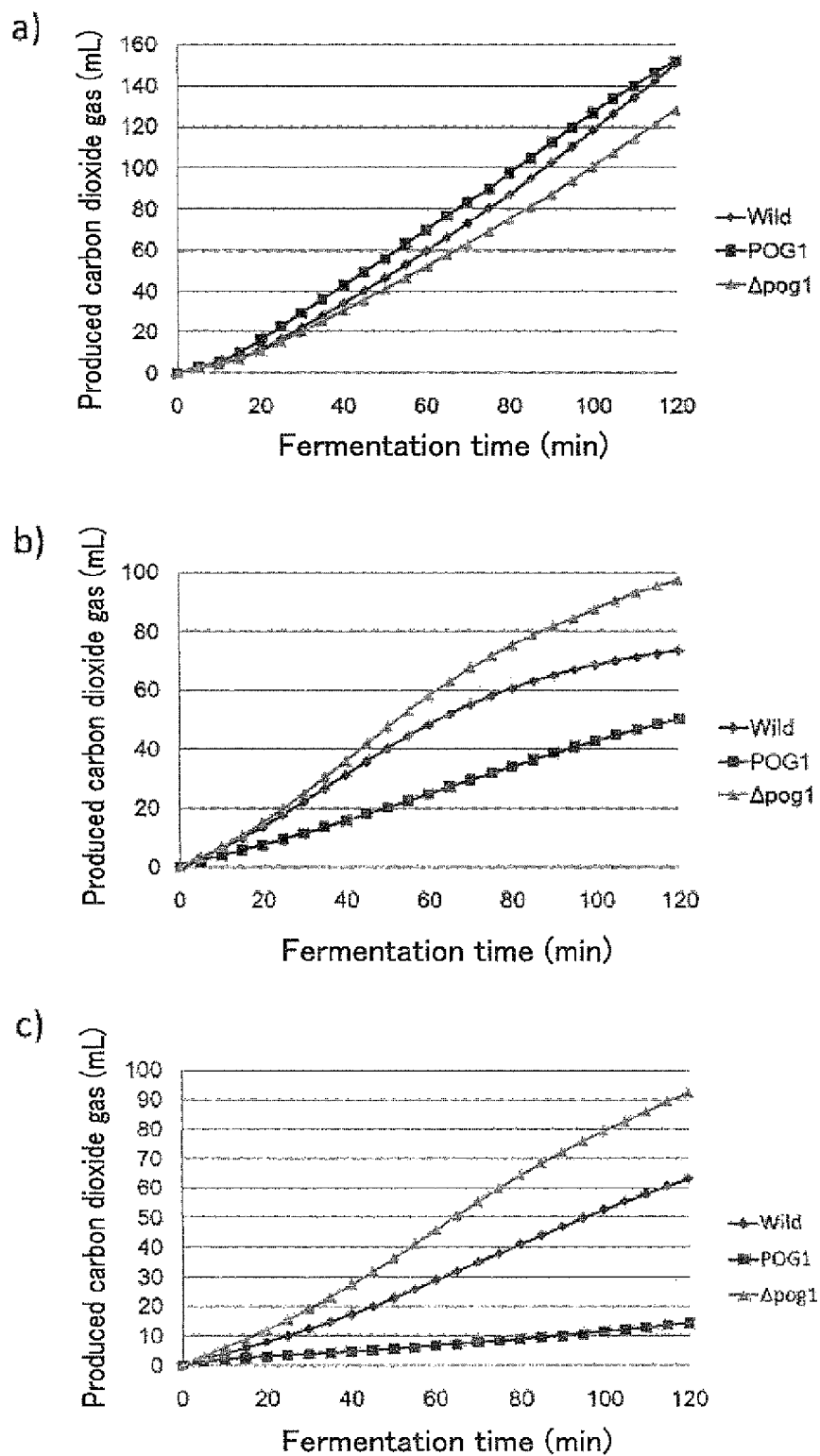
FIG. 3 shows the results of comparison of fermentation ability under a stress condition and a non-stress condition. a) the amount of carbon dioxide gas (mL) generated per hour under a non-stress condition; b) the amount of carbon dioxide gas (mL) generated per hour under a condition where thawing was performed one weeks after the freezing stress; c) the amount of carbon dioxide gas (mL) generated per hour under a condition where thawing was performed three weeks after the freezing stress. Wild shows a wild type strain; POG1 shows a strain highly expressing POG1 gene; Δpog1 shows a strain in which POG1 gene is disrupted.
Figure 4:
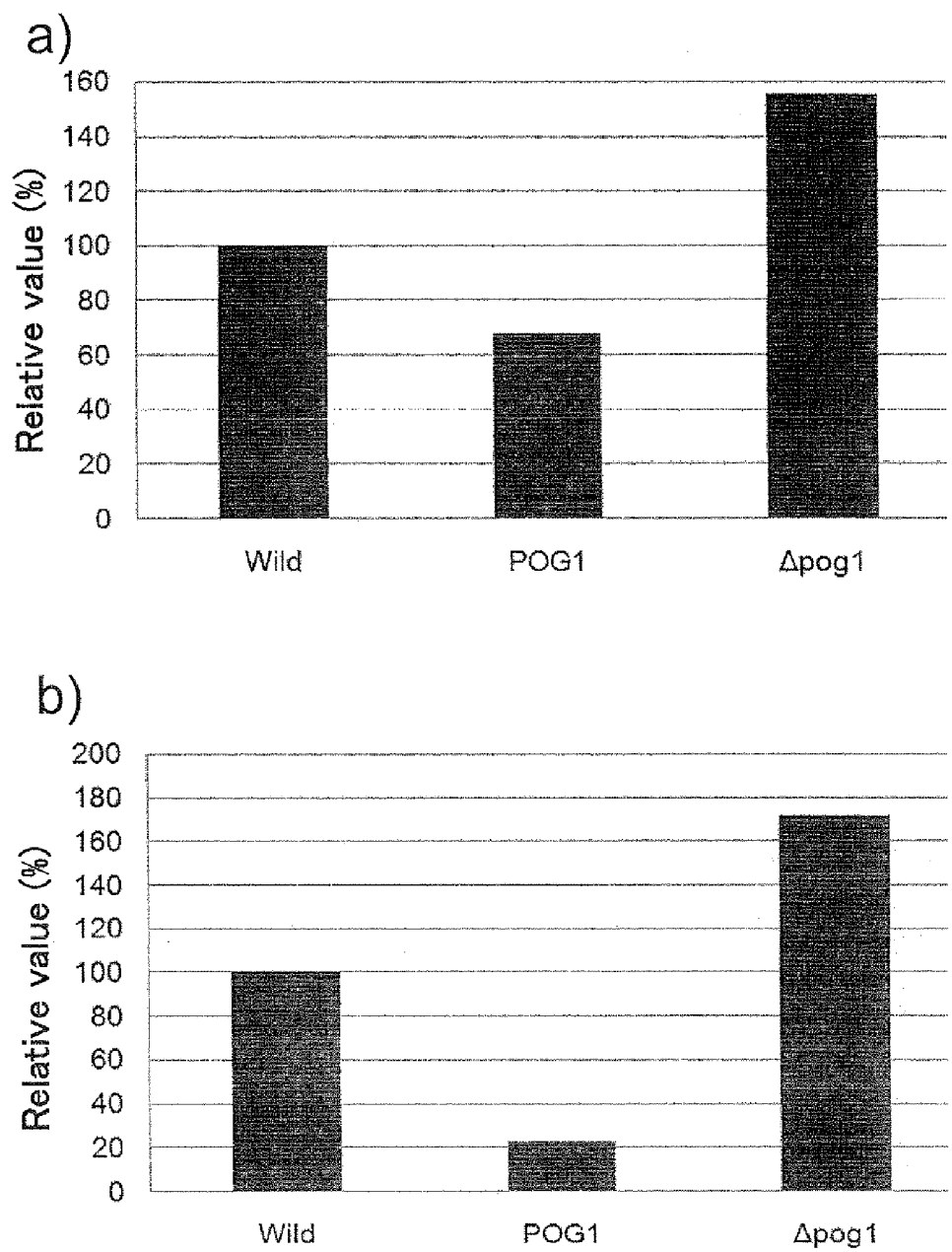
FIG. 4 shows the results of comparison of fermentation ability under a stress condition. The ratio of the amount of carbon dioxide gas produced by the wild type strain (Wild) under the freezing stress to that under the non-stress condition is determined to be 100. Comparison of the change of the ratio of the amount of carbon dioxide gas produced by the strain highly expressing POG1 gene (POG1) and the POG1 gene disrupted strain (Δpog1) before and after the freezing stress. a) shows the results under the condition where thawing was performed one week after the freezing stress; b) shows the results under the condition where thawing was performed three weeks after the freezing stress.

A wild type strain, the POG1 gene disrupted strain, and a POG1 gene highly expressing strain were cultured in a molasses medium (5.88% molasses, 0.214% urea, 0.051% Potassium dihydrogenphosphate) to a stationary phase, thereafter the cultured cells were dehydrated to a water content of 66% using a porcelain drying plate (Nikkato Co., Ltd.). Four grams of the yeast was added to high sugar content dough containing 5 g sucrose, 2 g sodium chloride, 68 mL water vs. 100 g flour for, bread dough. The mixture was mixed using a Swanson type mixer (National Mfg. Co., Ltd.) at 100 rpm for 3 minutes, thereafter the mixture was divided into 40 g each, and put into a screw cap bottle and sealed. Then, pre-fermentation was performed at 30° C. for 120 minutes, thereafter the whole bread dough was frozen at −20° C. One week or three weeks after the freezing, the amount of the produced carbon dioxide gas was measured after thawing at 30° C. for 30 minutes using Fermograph II (Atto Co., Ltd.). The results are shown in FIG. 3b), c) and FIG. 4a), b), respectively. The results obtained by measuring the amount of the produced carbon dioxide gas immediately after pre-fermentation without freezing are shown in FIG. 3a).

TABLE 1

Ratios of fermentation ability of the POG1 gene disrupted strain according to the present invention vs. that of the wild type strain.

| Strain | Pre-fermentation for 2 h 1 week after freezing stress | Pre-fermentation for 2 h 3 weeks after freezing stress |
|---|---|---|
| Wild type | 100 | 100 |
| POG1 gene highly expressing strain | 67.7 | 22.6 |
| POG1 gene disrupted strain | 155.5 | 171.5 |

The results show that fermentation ability of the POG1 gene disrupted diploid baker's yeast strain for practical use was significantly higher than that of the wild type strain by about 56% and about 72% after one week and three weeks after freezing, respectively. This shows that POG1 gene disruption is a suitable method for production of baker's yeast for practical use which is resistant to frozen dough.

INDUSTRIAL APPLICABILITY

The method of the present invention enables to isolate yeast having high fermentation ability even under a condition of freezing stress. By using such yeast, fermentation efficiency can be increased under a freezing circumstances such as in a method of production of bread using frozen dough where sufficient fermentation was difficult in the past.

SEQUENCE LISTING FREE TEXT

SEQ ID NOs: 3-8: Primers.

What is claimed is:

1. A method for producing yeast having increased resistance to freezing stress, comprising a step of inactivating POG1 gene, and further comprising a step of comparing resistance to freezing stress of yeast in which the POG1 gene is inactivated with that of yeast in which the POG1 gene is not inactivated, wherein the POG1 gene is inactivated in a yeast by disruption of the POG1 gene, introduction of a transposon into the POG1 gene, introduction of an antisense gene of the POG1 gene and its expression, introduction of a DNA which participates in silencing into a site near the POG1 gene, treatment by antibody to a polypeptide encoded by the POG1 gene, or submission of a yeast to a mutation treatment, and wherein the POG1 gene consists of any one of the following polynucleotides:

(a) a polynucleotide encoding the amino acid sequence of SEQ ID NO:1;

(b) a polynucleotide encoding a protein having a homology of 95% or more to the amino acid sequence of SEQ ID NO:1;

(c) a polynucleotide consisting of the nucleotide sequence of SEQ ID NO:2;

(d) a polynucleotide which hybridizes in stringent conditions to a polynucleotide consisting of a nucleotide sequence complementary to any polynucleotide of (a) or (c), wherein the stringent conditions are conditions where hybridization is done at 60-68° C. for 16-24 hours in a buffer solution consisting of 0.2M $Na_2PO_4$, pH 7.2, 7% SDS, 1 mM EDTA, and 1×Denhardt's solution, and washed twice for 15 minutes, at 60-68° C. in a buffer solution consisting of 20 mM $Na_2PO_4$, pH 7.2, 1% SDS, and 1 mM EDTA.

2. The method according to claim 1, further comprising a step of selecting yeast having increased resistance to freezing stress, wherein the selection is done using increased fermentation ability of the yeast under freezing stress as an indicator.

* * * * *

SEQUENCE LISTING

```
<160> NUMBER OF SEQ ID NOS: 8

<210> SEQ ID NO 1
<211> LENGTH: 351
<212> TYPE: PRT
<213> ORGANISM: Saccharomyces cerevisiae

<400> SEQUENCE: 1

Met Lys Gln Glu Pro His Arg Gln Ser Glu Glu Lys Glu Lys Pro Lys
1               5                   10                  15

Gly Pro Met Ala Val Glu Arg Glu Gln His Thr Ser Leu Ser Ser Gly
            20                  25                  30

Thr Thr Val Thr Ala Ser Thr Gly Asp Glu Ser Thr Asn Ser Arg Pro
```

```
                35                  40                  45
Val Glu Ser Ser Gln Thr Glu Lys Ser Leu Ser Leu Arg Ile Arg Ile
 50                  55                  60
Leu Lys Gln Leu Gly Phe Asp Asp Ile Gln Glu Leu Asn Ala Cys Asp
 65                  70                  75                  80
Thr Gly Leu Val Glu Gln Phe Leu Asn Val Arg Leu Ile Asn Asp Thr
                 85                  90                  95
Lys Glu Leu Glu Lys Ile Arg Glu Ser Asn Leu Ala Lys Leu Asn Gln
                100                 105                 110
Ile Ile Asp Lys Cys Met Glu Ser Asp Lys Ile Ser Asp Ser Thr Leu
            115                 120                 125
Asn Lys Ile Leu Asp Met Ser Met Asn Arg Asp Thr Asn Asn Asp Asn
130                 135                 140
Asn Asn His Leu Thr Ile Pro Ser Pro Ile Thr Thr Lys Lys Arg Lys
145                 150                 155                 160
Ile Asn Ala Ser Glu Leu Ala Ser Pro Arg Gly His Arg Arg Tyr Arg
                165                 170                 175
Ser Asp Ile Pro Thr Val Ser Glu Val Glu Thr Gly Val Gly Tyr Pro
                180                 185                 190
Gln Ile His Gln Gln Pro Gly Ala Tyr Thr Leu Pro Met Pro Ala Asn
            195                 200                 205
Gln Trp Met Ser Asn Pro Tyr Met Gln Pro Gln Pro Gln Val Gln
        210                 215                 220
Gln Ile Met Pro Gln Tyr Leu Tyr Pro Pro Gly Met Gly Pro Gln Ala
225                 230                 235                 240
Gln Leu Pro Thr Met Ser Ser Asn Ser Glu Ser Gln Thr Pro Val Met
                245                 250                 255
Ser Ser Gln Phe Leu Ser Leu Asn Gln His Gly Leu Tyr Gln Gln Asn
            260                 265                 270
Ile Gly Ala His Pro Val Met Ser Met Gly Pro Gln Ala Asn Ile Tyr
        275                 280                 285
Gly Gln Gln His Gln Leu Gln Pro Gly Gln Glu Arg Asp Gln Ser Arg
290                 295                 300
Lys Ser Phe Ser His Arg Arg Ser Gln Ser Ala Asn Ile Ser Met Ala
305                 310                 315                 320
Asn Phe Arg Ser Pro Met Arg Asn Pro Gln Pro Ala Ser Ser Gln Arg
                325                 330                 335
Pro Val Asn Phe Leu Ile His Thr Pro Lys His Pro Pro Pro Thr
            340                 345                 350

<210> SEQ ID NO 2
<211> LENGTH: 1056
<212> TYPE: DNA
<213> ORGANISM: Saccharomyces cerevisiae

<400> SEQUENCE: 2
atgaagcagg agccacatag acaatccgaa gaaaaagaga agccgaaagg accaatggct      60
gttgaacgag agcagcatac ctcattatct tctggtacaa ccgtgacagc tagtacagga     120
gacgagagta ccaacagtag accagtggaa tcatcgcaaa cagaaaagtc tctatcgctt     180
cgaataagaa tattaaaaca acttgggttt gacgatattc aagaactaaa tgcatgcgac     240
actggcctag tggagcaatt tttaaacgta cgattgataa acgacacaaa agaactagaa     300
aagatacgcg agtcaaatct tgcgaaacta accagatta ttgataaatg tatggaaagt     360
```

```
gataaaataa gtgattcgac attaaacaag attcttgata tgtccatgaa tagagataca    420
aataatgata acaacaatca tcttacgata ccgtctccga taacgacaaa gaaacgcaag    480
ataaacgcct ccgaacttgc aagtccacga ggccatagaa gatatagatc tgatatacct    540
acagtgtcag aagttgagac aggggtcgga taccctcaaa tacaccagca accaggcgca    600
tatactttac ctatgcctgc aaatcagtgg atgagcaacc cgtatatgca acctccgcaa    660
ccacaagtgc aacagataat gccgcagtat ttatatccac cagggatggg accacaagct    720
cagcttccta caatgagctc aaactcggag tcccagacac cagtgatgag ctcacagttt    780
ctttccttga accagcatgg cctttaccaa caaaatatag gtgctcatcc ggtaatgagt    840
atgggcccac aggcaaatat atacgggcag cagcaccagc tgcaacctgg tcaggaacga    900
gaccagtcaa gaaaagttt tagtcataga aggtcacaaa gtgccaatat ttccatggca    960
aattttaggt cgcccatgcg aaatccccag ccggcttcgt cccaaaggcc cgtcaattt    1020 ctcattcata caccaaaaca tcctcctccc acatga                             1056
```

```
<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ctagggaaga caagcaacga aacg                                           24

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
gggcgggtta tcagatatta tcagg                                          25

<210> SEQ ID NO 5
<211> LENGTH: 88
<212> TYPE: DNA
<213> ORGANISM: Artificial Sequence
<220> FEATURE:
<223> OTHER INFORMATION: primer

<400> SEQUENCE: 5
cctgcgctta actcatacaa aaaggcgcaa aacatttcaa gagtcccacg attaattgca    60
gaaattgaaa gattcggtaa tctccgag                                       88

<210> SEQ ID NO 6
<211> LENGTH: 94
<212> TYPE: DNA
<213> ORGANISM: Artificial Sequence
<220> FEATURE:
<223> OTHER INFORMATION: primer

<400> SEQUENCE: 6
tgaactgaag taaggtggac ggatgcatcg aatgaaggtt aggaagggat atagttttag    60
aaattaggtg gtaataactg atataattaa attg                                94

<210> SEQ ID NO 7
<211> LENGTH: 21
```

```
<212> TYPE: DNA
<213> ORGANISM: Artificial Sequence
<220> FEATURE:
<223> OTHER INFORMATION: primer

<400> SEQUENCE: 7
ttaaaggcta cgcagaagag g                                      21

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
ggcctctagg ttcctttgtt acttc                                  25
```